US011013221B2

(12) United States Patent
Nam et al.

(10) Patent No.: US 11,013,221 B2
(45) Date of Patent: May 25, 2021

(54) ANTI-AGING TRANSGENIC CAENORHABDITIS ELEGANS

(71) Applicants: POSTECH ACADEMY-INDUSTRY FOUNDATION, Pohang-si (KR); INSTITUTE FOR BASIC SCIENCE, Daejeon (KR); DAEGU GYEONGBUK INSTITUTE OF SCIENCE, Daegu (KR)

(72) Inventors: Hong Gil Nam, Seoul (KR); Gyoo Yeol Jung, Pohang-si (KR); Seung Jae Lee, Pohang-si (KR); Woo Seon Hwang, Pohang-si (KR); Gi Won Shin, Pohang-si (KR); Mi Hwa Seo, Seoul (KR)

(73) Assignees: POSTECH ACADEMY-INDUSTRY FOUNDATION, Pohang-si (KR); INSTITUTE FOR BASIC SCIENCE, Daejeon (KR); DAEGU GYEONGBUK INSTITUTE OF SCIENCE, Daegu (KR)

( * ) Notice: Subject to any disclaimer, the term of this patent is extended or adjusted under 35 U.S.C. 154(b) by 56 days.

(21) Appl. No.: 16/095,414

(22) PCT Filed: Apr. 21, 2017

(86) PCT No.: PCT/KR2017/004280
§ 371 (c)(1),
(2) Date: Oct. 22, 2018

(87) PCT Pub. No.: WO2017/188666
PCT Pub. Date: Nov. 2, 2017

(65) Prior Publication Data

US 2019/0200589 A1 Jul. 4, 2019

(30) Foreign Application Priority Data

Apr. 25, 2016 (KR) ........................ 10-2016-0049947

(51) Int. Cl.

| | |
|---|---|
| ***A01K 67/033*** | (2006.01) |
| ***G01N 33/50*** | (2006.01) |
| ***A01K 67/027*** | (2006.01) |
| ***C12N 15/85*** | (2006.01) |
| ***A61K 49/00*** | (2006.01) |
| ***C12N 15/113*** | (2010.01) |
| ***C12N 15/89*** | (2006.01) |
| *C12N 15/11* | (2006.01) |

(52) U.S. Cl.
CPC ........ *A01K 67/0336* (2013.01); *A01K 67/027* (2013.01); *A61K 49/0008* (2013.01); *C12N 15/113* (2013.01); *C12N 15/85* (2013.01); *C12N 15/89* (2013.01); *G01N 33/50* (2013.01); *A01K 2217/05* (2013.01); *A01K 2227/703* (2013.01); *A01K 2267/035* (2013.01); *C12N 15/11* (2013.01); *C12N 2330/51* (2013.01)

(58) Field of Classification Search
CPC .................................................. A01K 67/0336
See application file for complete search history.

(56) References Cited

U.S. PATENT DOCUMENTS

2014/0082757 A1 3/2014 Lee et al.

FOREIGN PATENT DOCUMENTS

KR 10-1606278 3/2016

OTHER PUBLICATIONS

Berkowitz et al. (2008, J. Visualized Experiments, e833, pp. 1-4) (Year: 2008).*
Chan et al. (1982, Nuclec Acids Res., Vo. 10(12), pp. 3755-3758). (Year: 1982).*
Lewis et al. (2002, Molecular Biology of the Cell, 4th Ed., Garland Science, pp. 1-24) (Year: 2002).*
Burga et al., 2012, FEBS J., vol. 279, pp. 3765-3775 (Year: 2012).*
Yuet, K. P. et al., "Cell-specific Proteomic Analysis in Caenorhabdit is Elegans", Proceedings of the National Academy of Sciences of the United States of America, [E-pub.] Feb. 17, 2015, vol. 112, No. 9, pp. 2705-2710.
Dewez, M. et al., "The Conserved Wobble Uridine tRNA Thiolase Ctu1-Ctn2 is Required to Maintain Genome Integrity", Proceedings of the National Academy of Sciences of the United States of America, [E-pub.] Apr. 7, 2008, vol. 105, No. 14, pp. 5459-5464.
Blanchet, S. et al., "New Insights into the Incorporation of Natural Suppressor tRNAs at Stop Codons in *Saccharomyces cerevisiae*", Nucleic Acids Research, [E-pub.] Jul. 23, 2014, vol. 42, No. 15, pp. 10061-10072.
Lee, Y. S. et al., "A novel class of small RNAs: tRNA-derived RNA fragments (tRFs)", Genes & Development, vol. 23, No. 22, pp. 2639-2649, Nov. 15, 2009.
KIPO, Notice of Allowance of KR 10-2016-0049947 dated Mar. 29, 2018.

* cited by examiner

*Primary Examiner* — Thaian N. Ton
*Assistant Examiner* — David A. Montanari
(74) *Attorney, Agent, or Firm* — Lex IP Meister, PLLC

(57) ABSTRACT

The present invention relates to: a transgenic *Caenorhabditis elegans* in which a glutamine tRNA 5' terminus-derived fragment (Gln 5'-tsRNA) is overexpressed; a preparation method therefor; and a method for screening for aging-associated factors by using the transgenic *Caenorhabditis elegans*. A transgenic *Caenorhabditis elegans* model provided in the present invention is an animal model in which Gln 5'-tsRNA is overexpressed such that aging is inhibited. When the model of the present invention is used, anti-aging mechanisms can be easily investigated, thereby significantly contributing to various research fields such as that of developing new anti-aging drugs and screening for age-inducing materials.

6 Claims, 7 Drawing Sheets

Specification includes a Sequence Listing.

【FIG. 1】
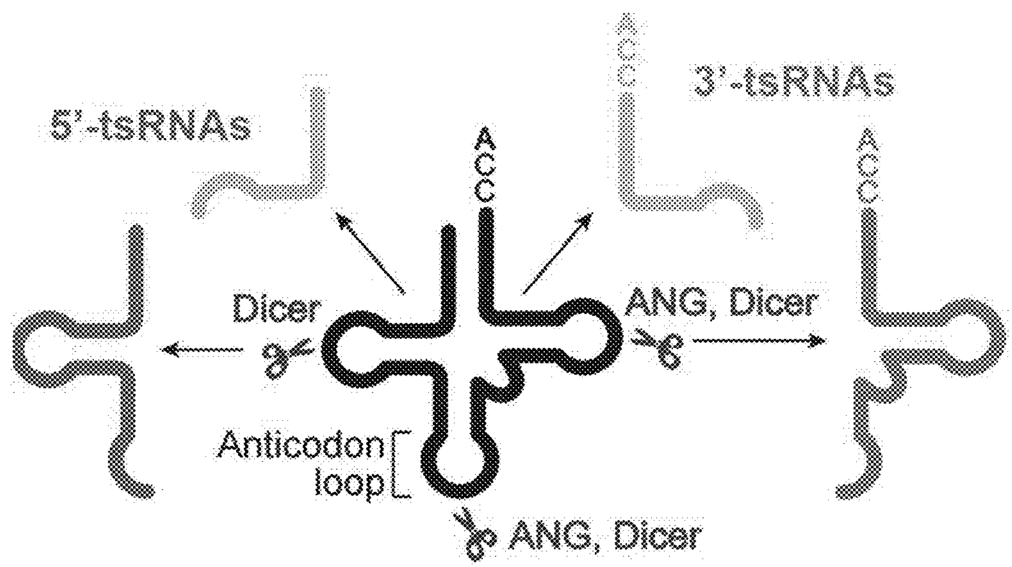
【FIG. 2】
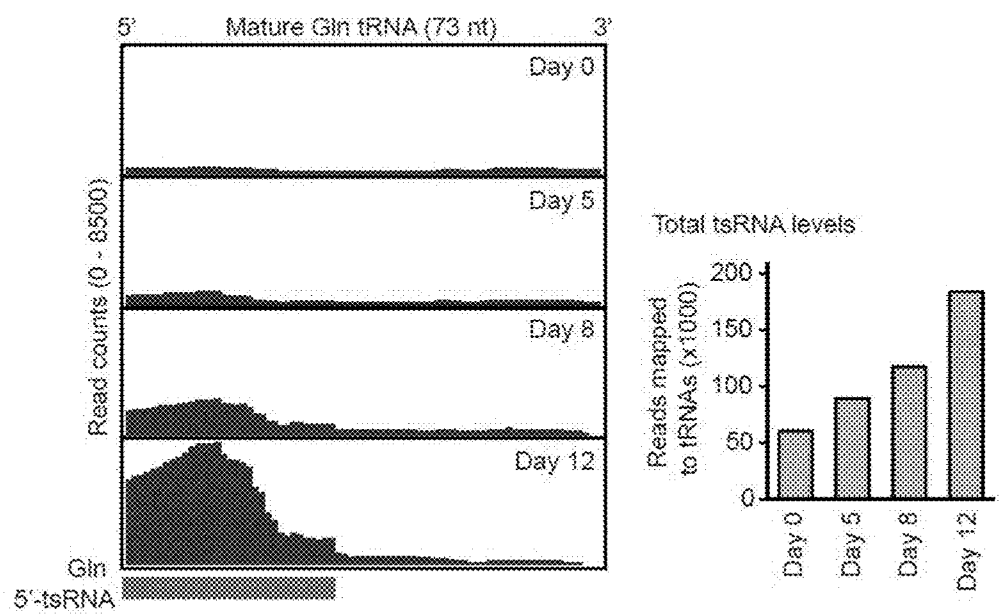

【FIG. 3】
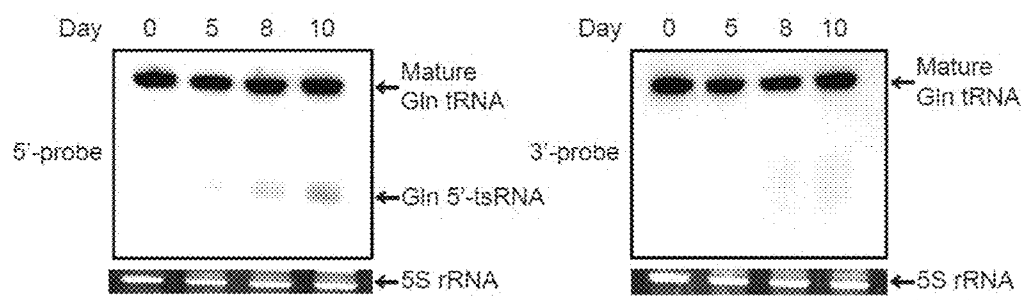
【FIG. 4】
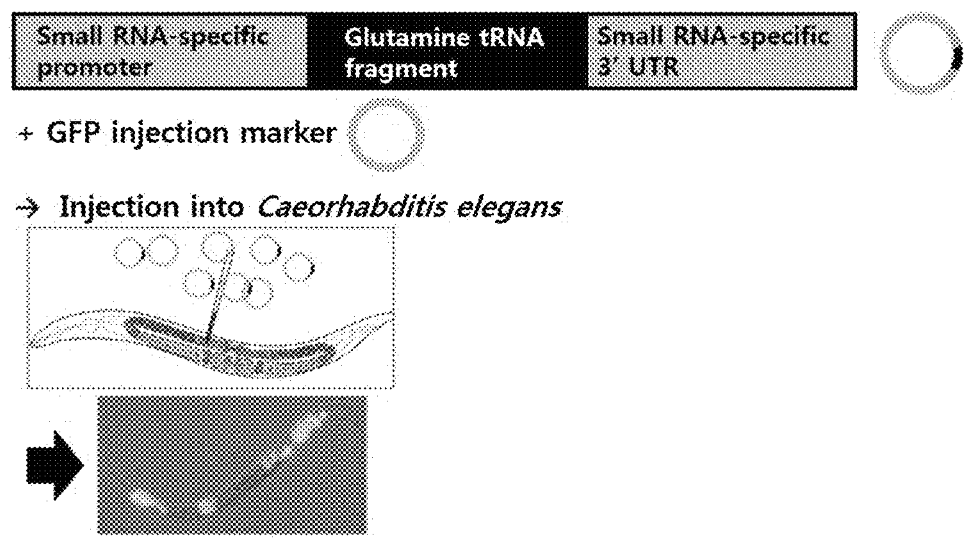
*Caeorhabditis elegans* in which Gln 5'-tsRNA is overexpressed 【FIG. 5】
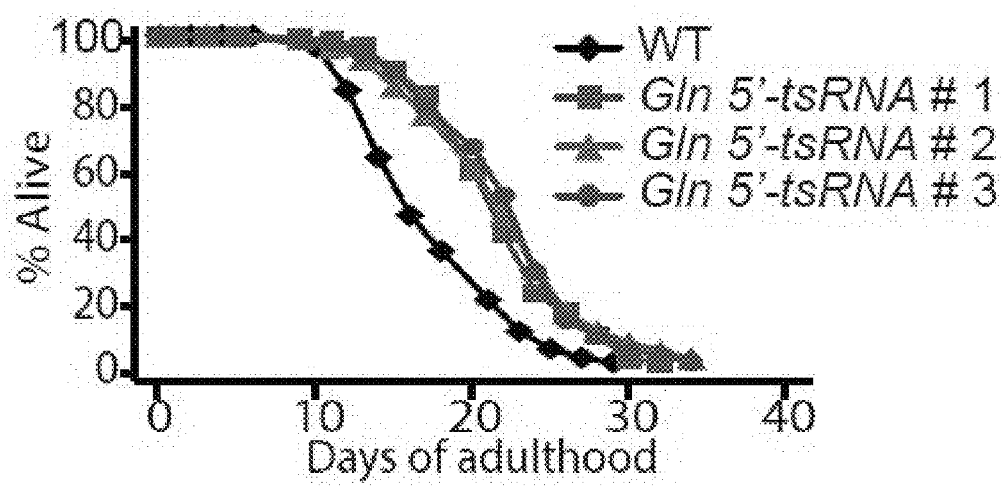
【FIG. 6】
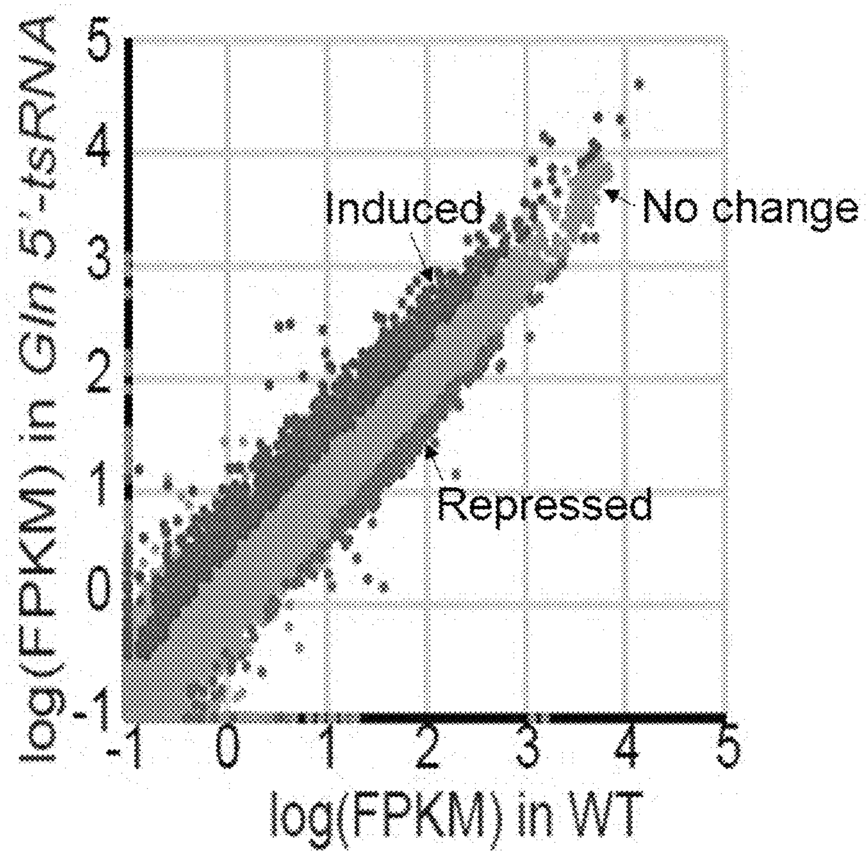

【FIG. 7】
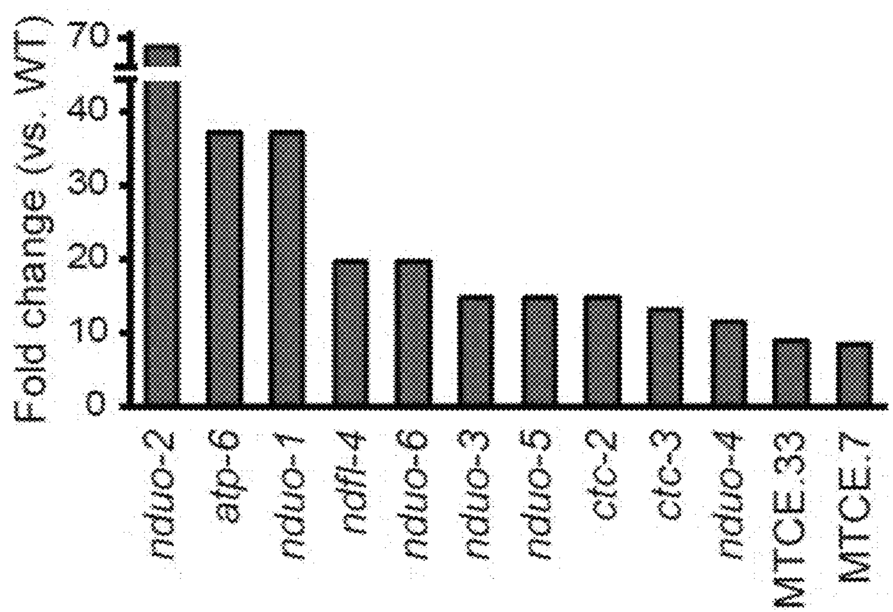
【FIG. 8】
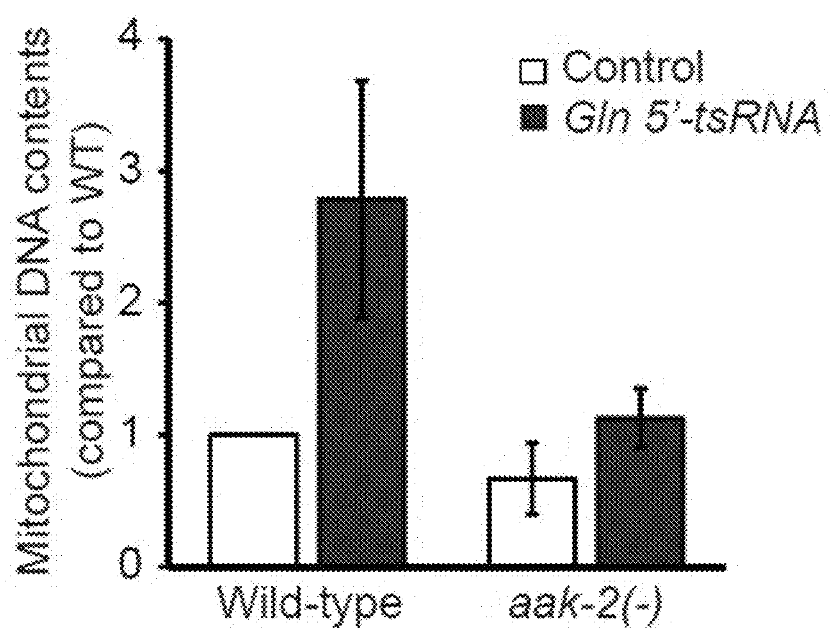

【FIG. 9A】
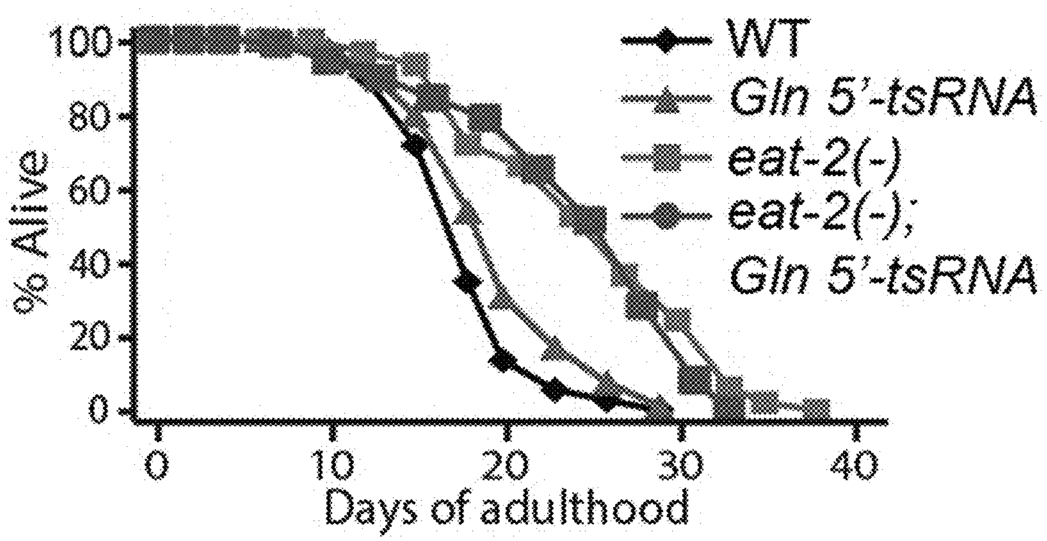
【FIG. 9B】
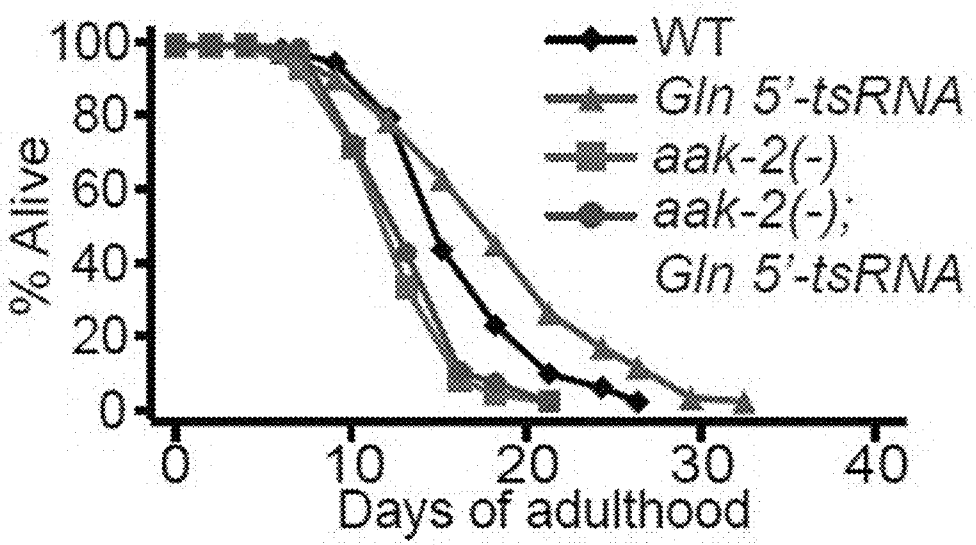

【FIG. 9C】
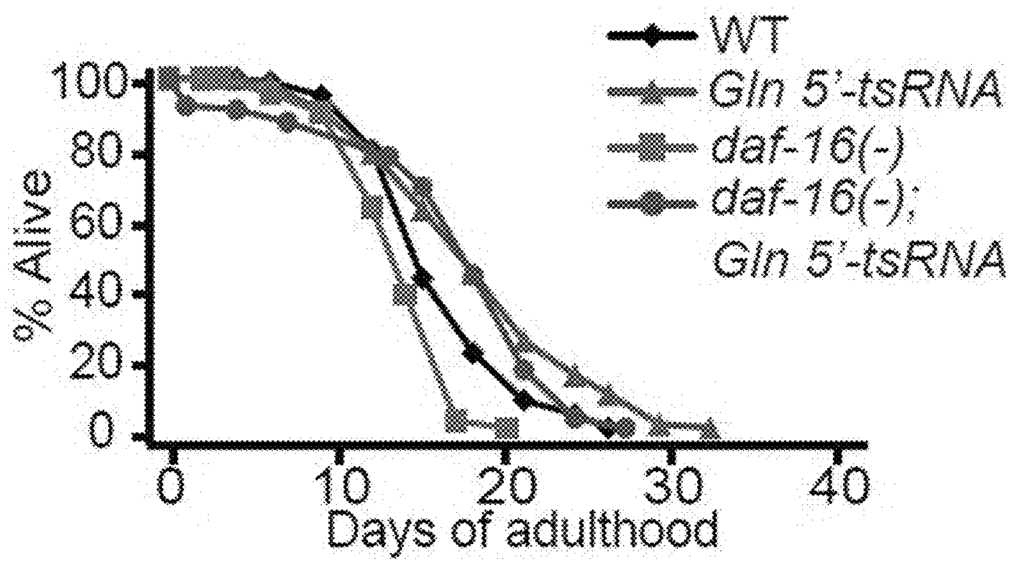
【FIG. 9D】
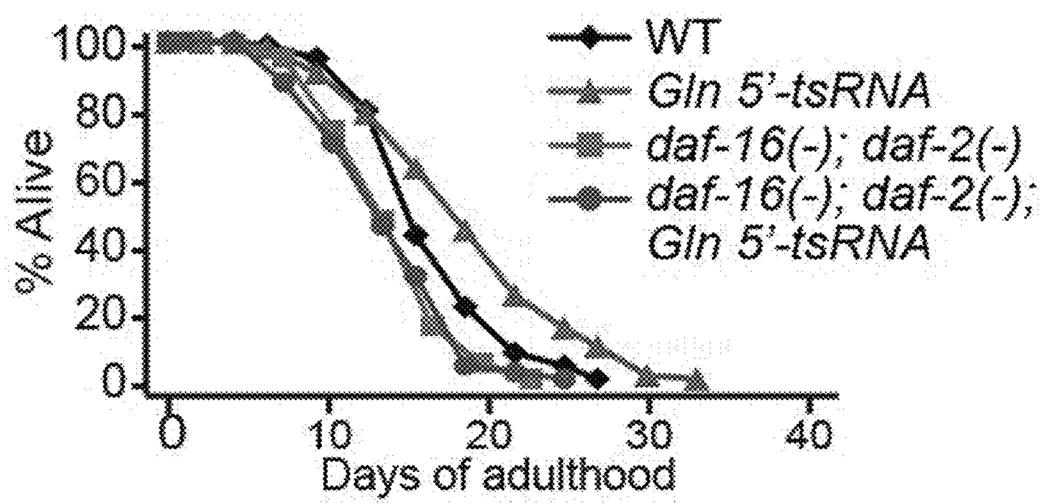

【FIG. 9E】
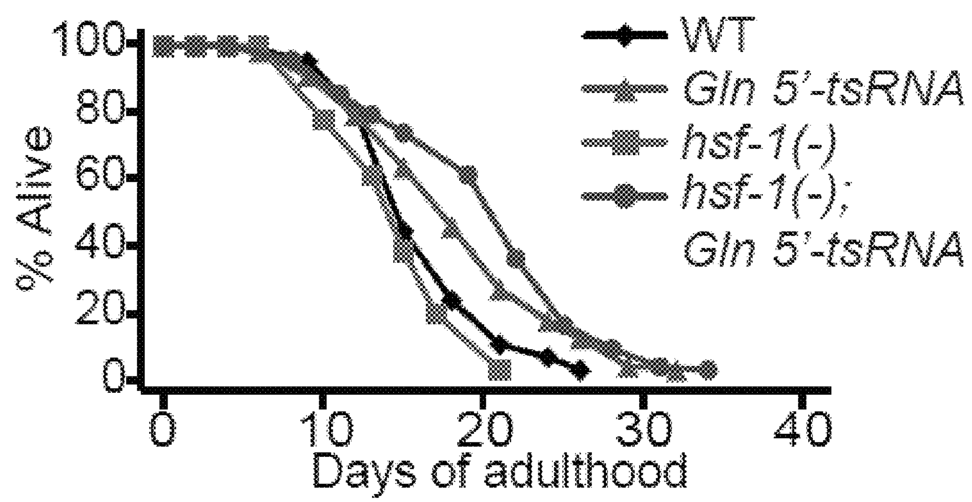

ANTI-AGING TRANSGENIC CAENORHABDITIS ELEGANS

TECHNICAL FIELD

The present invention relates to transgenic *Caenorhabditis elegans* (*C. elegans*) in which a glutamine tRNA 5' end-derived fragment (Gln 5'-tsRNA) is overexpressed, a method of constructing the same, and a method of screening an aging-related factor using the transgenic *C. elegans.*

BACKGROUND ART

Small non-coding RNA of approximately 20 to 50 bp is RNA serving as RNA itself, unlike mRNA expressed into a protein, and it has recently been identified that various small RNAs play important functions in a living body. The small RNAs include microRNA (miRNA), small interfering RNA (siRNA), and PIWI-binding RNA (piRNA), and serve to interfere with and suppress RNA targets having base sequences complementary to their own base sequences.

tRNA-derived fragments (tRNA-derived small RNAs; tsRNAs) are a type of small non-coding RNAs newly found in various subjects. These fragments are found in various species including a rat, *C. elegans, Arabidopsis thaliana*, as well as a human, and thus it is assumed that they have evolutionarily conserved functions. In addition, since tsRNAs are generated by cleaving a specific part from previously-made mature tRNA, and found only as a specific base sequence, not an arbitrary base sequence, tsRNA is considered to be a fragment having a specific function rather than a fragment simply produced by randomly degrading tRNA. Here, four types of fragments may be produced according to cleaved sites in mature tRNA, and classified into, for example, 5'-tsRNA, 3' CCA tsRNA, 3' U tsRNA, and internal tsRNA (see FIG. 1).

tsRNAs have been found in cancer cell lines, virus-infected cells, adipose tissue-derived stem cells, and mouse serum, fragments are generated in various physiological circumstances such as stress, etc. Since it has been reported that they have regulatory functions similar to small RNA, anti-aging-related functions have not been identified yet.

Particularly, due to the characteristics of a tRNA gene, there is difficulty in sequencing of tsRNAs, and for example, since multiple copies of the tRNA gene are present in the entire genome, some of the multiple copies are the same, but some differ in sequence, it is difficult to confirm an exact genomic origin from which tsRNA is derived. In addition, since mature tRNA is severely modified, it is difficult to exactly match a genomic sequence corresponding to tsRNA generated from the mature form.

Meanwhile, since *C. elegans* only takes approximately three days from being hatched from an egg to becoming an adult via four stages of larval phase including L1, L2, L3 and L4, and has a lifespan of approximately 3 weeks, it is an animal model suitable for a developmental experiment or lifespan experiment. In addition, *C. elegans* facilitates genetic manipulation, has a small size, is grown relatively economically in a large quantity at once, and has a transparent body, and therefore it is very easy to directly observe the inside of *C. elegans* or to observe fluorescence using a microscope.

In addition, *C. elegans* conserves many genes involved in human diseases, and thus the potential of discovering and analyzing genes using this worm and developing a new drug targeting these genes has been investigated. For example, genes involved in an insulin signaling pathway, apoptosis-regulating genes, and MAP kinase signaling pathway genes critical for immune regulation, which are genes critical for regulation of metabolism and aging in mammals, are also present in *C. elegans*, and the mechanisms of these genes have been actively studied.

DISCLOSURE

Technical Problem

Therefore, under the premise that *C. elegans* can be a favorable animal model for facilitating genetic manipulation and identifying an anti-aging mechanism and a pathological role, the inventors found that the level of specific tsRNA in *C. elegans* is age-dependently changed, and constructed transgenic *C. elegans* animals in which specific tRNA-derived fragments (tsRNAs) are overexpressed by taking note of relationship between tsRNAs and aging/lifespan.

Accordingly, an object of the present invention is directed to providing transgenic *C. elegans* in which a glutamine tRNA 5' end-derived fragment (Gln 5'-tsRNA) is overexpressed, a method of constructing the same, and a method of screening an aging-related factor using the transgenic *C. elegans.*

However, technical problems to be solved in the present invention are not limited to the above-described problems, and other problems which are not described herein will be fully understood by those of ordinary skill in the art from the following descriptions.

Technical Solution

The present invention provides transgenic *C. elegans* in which a glutamine tRNA 5' end-derived fragment (Gln 5'-tsRNA) is overexpressed.

In an exemplary embodiment of the present invention, the *C. elegans* is an anti-aging animal model.

In another exemplary embodiment of the present invention, the Gln 5'-tsRNA consists of a base sequence of SEQ ID NO: 1.

In still another exemplary embodiment of the present invention, the *C. elegans* exhibits an anti-aging effect by mitochondria activation.

In yet another exemplary embodiment of the present invention, the *C. elegans* exhibits an anti-aging effect by dietary restriction (DR)/AMP-dependent kinase (AMPK) pathways.

The present invention also provides a method of constructing the transgenic *C. elegans*, the method including: (a) preparing a recombinant vector including an U6 promoter, Gln 5'-tsRNA DNA and a U6 3' untranslated region (UTR); and (b) injecting the recombinant vector into *C. elegans.*

In one exemplary embodiment of the present invention, in the operation (a), the U6 promoter is a promoter specific for small RNA overexpression.

In another exemplary embodiment of the present invention, in the operation (b), a method of injecting the recombinant vector into *C. elegans* is microinjection.

In addition, the present invention provides a method of screening an aging-inducing candidate material using the transgenic *C. elegans.*

In one exemplary embodiment of the present invention, the screening method includes: (a) treating the transgenic *C. elegans* with candidate materials; (b) following the treatment of the candidate materials, measuring mitochondrial activity; and (c) selecting a candidate material with lower mitochondrial activity than a control group not treated with the candidate material.

In another exemplary embodiment of the present invention, the screening method includes: (a) treating the transgenic *C. elegans* with candidate materials; (b) following the treatment of the candidate materials, measuring AMPK activity; and (c) selecting a candidate material with lower AMPK activity than a control group not treated with the candidate material.

Advantageous Effects

Transgenic *C. elegans* model provided in the present invention is an animal model in which aging is suppressed by overexpression of a glutamine tRNA 5' end-derived fragment (Gln 5'-tsRNA), and using this model of the present invention, an anti-aging mechanism can be easily identified.

In addition, a method of constructing anti-aging transgenic *C. elegans* provided in the present invention employs a promoter specific for overexpression of small RNA, such as tRNA-fragmented RNA, which is not a common protein, and by using the above-described method, *C. elegans* overexpressing a variety of small RNAs can be easily constructed.

Moreover, as anti-aging functions of tsRNAs are identified, the present invention can be expected to highly contribute to various research fields such as development of a new anti-aging drug, and screening of various factors including an aging-inducing material.

DESCRIPTION OF DRAWINGS

FIG. 1 is a schematic diagram illustrating that four types of tsRNAs are generated according to cleaved sites in mature tRNA.

FIG. 2 shows a result confirming that Gln 5'-tsRNA increases according to age through *C. elegans* small RNA sequencing database analysis.

FIG. 3 shows Northern blotting results indicating that mRNA of glutamine 5'-tsRNA increases according to age in *C. elegans* samples.

FIG. 4 is a schematic diagram illustrating a process of constructing a Gln 5'-tsRNA-overexpressing transgenic *C. elegans* model using a small RNA-specific U6 promoter.

FIG. 5 shows the result of comparing lifespans between the Gln 5'-tsRNA tsRNA-overexpressing transgenic *C. elegans* and a wild-type to confirm the function of Gln 5'-tsRNA in aging.

FIG. 6 shows the result of confirming a change in mRNA profile induced by the overexpression of Gln 5'-tsRNA.

FIG. 7 shows the result of RNA sequencing analysis, confirming that mRNA levels of mitochondrial genes are much higher than that of a wild-type due to the overexpression of Gln 5'-tsRNA.

FIG. 8 shows the qPCR result confirming that DNA copy number of a mitochondrial gene in Gln 5'-tsRNA-overexpressing *C. elegans* is increased due to aak-2.

FIG. 9 shows the results of confirming genetic interactions between conventionally-known lifespan regulating pathways (DR, insulin/IGF-1 pathway, etc.) and the overexpression of Gln 5'-tsRNA, and specifically, shows the results of measuring changes in lifespan of Gln 5'-tsRNA-overexpressing *C. elegans* in an eat-2(−) mutation background (FIG. 9A), an aak-2(−) mutation background (FIG. 9B), a daf-16(−) mutation background (FIG. 9C), a daf-16 (−) mutation background; daf-2(−) mutation background (FIG. 9D), and a hsf-1(−) mutation background (FIG. 9E).

MODES OF THE INVENTION

The present invention provides transgenic *C. elegans* in which a glutamine tRNA 5' end-derived fragment (Gln 5'-tsRNA) is overexpressed.

The "*C. elegans*" used herein is *Caenorhabditis elegans* (scientific name), and is a nematode that feeds on bacteria in soil and is widely used in genetic, molecular biological, and cell biological experiments.

The "transformation" used herein means that an exogenously-introduced gene is recombined to be artificially inserted into a subject, thereby changing some of the subject's genetic traits.

The "transgenic *C. elegans*" used herein refers to *C. elegans* in which Gln 5'-tsRNA is overexpressed and thus aging is suppressed, that is, an anti-aging characteristic is exhibited, and therefore, the transgenic *C. elegans* of the present invention may be used for an anti-aging animal model.

The "tRNA-derived fragments (tRNA-derived small RNAs; tsRNAs)" used herein refers to a type of small non-coding RNAs, and fragments of specific base sequences generated by cleaving mature tRNA at a specific site.

The "Gln 5'-tsRNA" used herein is a fragment derived from the 5' end of glutamine tRNA, which is not particularly limited, and may be a fragment consisting of a base sequence of SEQ ID NO: 1 or having 80% or more homology. Here, the "homology" means that a fragment is naturally or artificially derived from a nucleic acid sequence derived from the common ancestor, and can be modified to include one or more selector codons by any available mutagenesis of any naturally-occurring nucleic acid.

The term "~derived from" used herein means that a component which is isolated from using a specified molecule or organism, or prepared using the information from it.

In the present invention, *C. elegans* for an anti-aging animal model is not particularly limited as long as it expresses an anti-aging characteristic regardless of the type of a mechanism, and the expression of the anti-aging characteristic may be caused by mitochondria activation or AMPK activity.

Here, mitochondria are cell organelles generating energy in vivo, play an important role in a variety of genetic diseases/adult diseases, and it has been reported that, when the mitochondria produce energy well to help smoothly progress energy metabolism, that is, when the mitochondria are activated, aging is suppressed. In addition, AMPK is a major enzyme that regulates energy homeostasis in a body, and an evolutionarily well-conserved enzyme expressed in most animal tissues. AMPK is associated with aging, which is a symptom accompanied by declination of normal functions of various organs, and since aging induces the occurrence of various diseases such as diabetes type II, neurodegenerative diseases, cancer, cardiovascular diseases, and death resulting therefrom, the potential to develop a new drug using a material that increases or decreases AMPK activity is very large, and can be utilized in various ways.

In addition, the present invention provides a method of constructing the transgenic *C. elegans*, which includes: (a) preparing a recombinant vector including a U6 promoter, Gln 5'-tsRNA DNA and a U6 3' untranslated region (UTR); and (b) injecting the recombinant vector into *C. elegans.*

In the present invention, the "recombinant vector" is a vector used in genetic engineering, which is, but not limited to, preferably a plasmid vector. The recombinant vector may be, for example, a virus vector, a cosmid vector, a bacterial artificial chromosome (BAC), a yeast artificial chromosome (YAC) or other non-plasmid vectors.

In the present invention, the recombinant vector may further include a marker gene that can confirm transformation. There is no particular limitation to the marker gene, and the marker gene is preferably a fluorescent protein gene such as a green fluorescent protein (GFP) gene or a red fluorescent protein (RFP) gene.

The "promoter" used herein refers to a DNA sequence which regulates expression of a nucleic acid sequence operably linked to specific host cells, and is not particularly limited as long as it is used for expression. The promoter is preferably a U6 promoter suitable for expression of small RNA. In addition, the "operably linked" means that one nucleic acid fragment is combined with another nucleic acid fragment so that its function or expression is affected by the other nucleic acid fragment.

In addition, the recombinant vector of the present invention may further include an arbitrary operator sequence for regulating transcription, a sequence encoding a suitable mRNA-ribosome binding site and a sequence that regulates the termination of transcription and translation.

DNA of Gln 5'-tsRNA introduced into the recombinant vector may be arranged to correspond to a transcription direction of the promoter present in a vector to effectively induce the expression of each gene by activity of the promoter.

In the present invention, a method of injecting the recombinant vector into *C. elegans* may be any method known in the art without limitation, and the method is preferably microinjection using a micropipette.

In addition, the present invention provides a method of screening an aging-inducing candidate material using the transgenic *C. elegans*.

Although there is no limitation to the method of screening an aging-inducing candidate material in the present invention, it is preferable to treat the transgenic *C. elegans* with a candidate material, and then measure mitochondrial activity or AMPK activity to select a candidate material with lower activity than the control group not treated with the candidate material.

According to the screening method of the present invention, searching for an aging-related factor (a gene or a drug) may be rapidly and easily performed, and thus it can contribute greatly to the study of many diseases associated with aging or to the development of new drugs.

Hereinafter, preferable examples are provided to help in understanding the present invention. However, the following examples are provided to more easily understand the present invention and the scope of the present invention is not limited by the following examples.

EXAMPLE 1

Culture of *C. elegans*

After purchase of a standard wild-type Bristol strain N2, *C. elegans* was cultured in an *E. coli* (OP50)-seeded nematode growth medium (NGM) agar plate at 20° C.

EXAMPLE 2

Confirmation of Change in tsRNA Level According to Age of *C. elegans*

A small RNA sequencing result according to the age of *C. elegans* was used to analyze how the tsRNA level was changed.

Specifically, using the modENCODE (http://data.modencode.org/Organism=*C. elegans*) database, an RNA read sequence obtained by sequencing was matched to each tRNA sequence of the tRNA database so as to analyze which read sequence in each part of specific tRNA is identified.

Consequently, as shown in FIG. 2, it was confirmed that a glutamine tRNA-derived fragment (Gln tsRNA), particularly, the read sequence of the 5' end, was age-dependently increased. Afterward, by sequencing the fragment using the known method, it was confirmed that the fragment consists of the base sequence of SEQ ID NO: 1.

```
                                      [SEQ ID NO: 1]
5'-GGTTCCATGGTGTAGCGGTTAGCACTCAGGACT-3'
```

EXAMPLE 3

Reconfirm that Gln 5'-tsRNA was Age-Dependently Increased in *C. elegans*

To reconfirm the result of Example 1 using a database, Northern blotting was performed to confirm whether a glutamine tRNA-derived fragment was actually increased according to aging in *C. elegans* samples.

Specifically, ten 60-mm plates of each *C. elegans* sample at the age of 0, 5, 8 or 10 days were collected to extract total RNA, and then Northern blotting was performed using respective probes specific for the 5' end and the 3' end of the glutamine tRNA. At this time, information on each probe used herein is shown below.

```
Probe for the 5' end of glutamine tRNA:
                                   (SEQ ID NO: 2)
5'-CCTGAGTGCTAACCGCTACACCATGGAACC-3'

Probe for the 3' end of glutamine tRNA:
                                   (SEQ ID NO: 3)
5'-TGGAGGTTCCACCGAGATTTGAACTCGGGT-3'
```

Consequently, as shown in FIG. 3, it can be confirmed that the fragment at the 5' end of the glutamine tRNA-derived fragment was increased according to age, which is the same as the result of Example 1.

EXAMPLE 4

Construction of Gln 5'-tsRNA-Overexpressing *C. elegans*

Based on the result of Example 3, to identify the relationship between Gln 5'-tsRNA and aging in vivo, a Gln 5'-tsRNA-overexpressing transgenic *C. elegans* model was constructed.

To this end, as shown in FIG. 4, a recombinant vector including an U6 promoter which is specific for overexpression of small RNA of *C. elegans*, Gln 5'-tsRNA and U6 3' UTR, was constructed. Specifically, the U6 promoter-Gln 5'-tsRNA and the Gln 5'-tsRNA-U6 3' UTR were amplified by PCR, a U6 promoter-Gln 5'-tsRNA-U6 3' UTR construct was constructed using PCR fusion, and then this construct was cloned in a pUC57 vector using EcoRI and HindIII restriction enzymes. Here, information on each primer used in the PCR is shown below.

```
Forward U6p:
                                             (SEQ ID NO: 4)
5'-CGGGAATTCCTCCAAGAACTCGTACAAAAATGCTCT-3'

Reverse U6p-Gln tsRNA:
                                             (SEQ ID NO: 5)
5'-AGTCCTGAGTGCTAACCGCTACACCATGGAACCAAACATTTAGATTT

GCAATTCAATTATATAGG-3'

Forward Gln tsRNA-U6UTR:
                                             (SEQ ID NO: 6)
5'-GGTTCCATGGTGTAGCGGTTAGCACTCAGGACTCAATAATATTCTAG

ATATCCCTTTTTG-3'

Reverse U6UTR:
                                             (SEQ ID NO: 7)
5'-CGGAAGCTTCACAGCCGACTATGTTTGGCGT-3'
```

Afterward, the recombinant vector was overexpressed by microinjecting into a reproductive organ of *C. elegans* along with a green fluorescence protein (GFP) marker, and then green fluorescence was observed using a fluorescent microscope to confirm whether DNA was contained.

Consequently, as shown in FIG. 4, it was confirmed that strong green fluorescence was exhibited in *C. elegans.*

EXAMPLE 5

Measurement of Lifespan of Gln 5'-tsRNA-Expressing *C. elegans*

Using the Gln 5'-tsRNA-overexpressing *C. elegans* constructed in Example 4, the function of the Gln 5'-tsRNA on aging was assessed by measuring the lifespan of *C. elegans.*

Specifically, *E. coli* OP50 was cultured in LB broth containing streptomycin for 12 to 16 hours at 37° C., and then plated in a NGM medium. After approximately 12 to 16 hours, *E. coli* OP50 was treated with 5 μM 5-fluoro-2'-deoxyuridine (FUdR), and 30 animals each of Gln 5'-tsRNA-overexpressing *C. elegans* (Young-adult stage) and a control group (wild-type) were plated on each of four plates. Then, the number of living *C. elegans* was counted once every two to three days to measure the lifespan of *C. elegans.*

Consequently, as shown in FIG. 5, it was confirmed that all of three types of glutamine tRNA 5' end-derived fragment (Gln 5'-tsRNA)-overexpressing (transformed) *C. elegans* lines had a longer lifespan than the control group (wild-type (WT)).

Since this result shows that overexpression of specific tsRNA can extend the lifespan of *C. elegans*, it means that tsRNA is a material that actively regulates aging/lifespan, not simply a passive byproduct of aging.

In addition, when associating the result of Example 5 with data of Examples 2 and 3, it can be seen that Gln 5'-tsRNA is a compensation mechanism for extending a lifespan by delaying aging, and thus is age-dependently increased in *C. elegans.*

EXAMPLE 6

Identification of Anti-Aging Mechanism of Gln 5'-tsRNA 6-1. Gene Screening

It was intended to identify an anti-aging mechanism by confirming how a gene is actually changed by overexpression of Gln 5'-tsRNA using the Gln 5'-tsRNA-overexpressing *C. elegans* constructed in Example 4.

First, since tsRNAs are known to regulate mRNA transcription, a change in mRNA profile, induced by Gln 5'-tsRNA overexpression was observed through RNA sequencing analysis.

Specifically, three independent sets of samples were prepared by bulk culturing wild-type *C. elegans* (control group) and Gln 5'-tsRNA-overexpressing *C. elegans* at day 1 adult stage, total RNA was extracted by a TRIzol base method, and then the quality of each sample was determined by RNA electrophoresis and qRT-PCR. Afterward, raw data obtained by RNA sequencing was analyzed using the Cufflinks pipeline.

Consequently, as shown in FIG. 6, it was confirmed that, compared with the wild-type *C. elegans,* 1261 types of genes were up-regulated, and 425 types of genes were down-regulated.

Afterward, as a result of comparing these genes (DEG: differentially expressed genes) with other known longevity mutant *C. elegans*, it can be seen that the DEGs considerably overlapped genes up-regulated by overexpression of an activated AMP-dependent kinase (AMPK), and genes up-regulated by daf-2(−)/insulin/insulin-like growth factor 1 (IGF-1) receptor mutations. This analysis result means that it is possible for Gln 5'-tsRNA to act together with an AMPK or insulin/IGF-1 signaling pathway.

In addition, according to an RNA sequencing analysis result, as shown in FIG. 7, it was confirmed that mRNA levels of mitochondrial genes are greatly increased by overexpression of Gln 5'-tsRNA, compared with a wild-type.

Further, according to quantitative PCR (qPCR), as shown in FIG. 8, it was observed that the mitochondrial DNA copy number was also increased. It can be seen that the effect of increasing the mitochondrial DNA copy number due to Gln 5'-tsRNA overexpression disappeared through the aak-2 mutation, indicating that the Gln 5'-tsRNA overexpression resulted in increasing the mitochondrial DNA copy number through AMPK.

Since DR is known to activate mitochondrial functions in various species, this result can be understood as Gln 5'-tsRNA and DR act together to promote the function of mitochondria to extend a lifespan.

6-2. Identification of Anti-Aging Mechanism

In order to confirm genetic interactions between conventionally known lifespan regulating pathways (DR, insulin/IGF-1 pathway, etc.) and the overexpression of Gln 5'-tsRNA, changes in the lifespan of Gln 5'-tsRNA-overexpressing *C. elegans* were determined under DR mimetic eat-2(−), insulin/IGF-1 receptor mutant daf-2(−), catalytic alpha subunit of AMPK mutant aak-2(−), fork head box O(FOXO) transcription factor mutant daf-16(−), heat-shock transcription factor 1 (HSF-1) mutant hsf-1(−) backgrounds.

Specifically, five long-living adult *C. elegans* were plated on a NGM medium and synchronized for 16 hours, and then when eggs were grown up to young-adult stages, they were transferred to a 5 μM FUdR-treated NGM medium twice every two days. During the final transfer, 120 animals per each background were selected, and then the number of living animals was counted every two to three days until all animals died, resulting in observation of a lifespan change.

Consequently, as shown in FIG. 9A, the overexpression of Gln 5'-tsRNA did not amplify the life-extending (anti-aging) effect of eat-2(−).

In addition, as shown in FIG. 9B, it can be seen that the lifespan extended by the overexpression of Gln 5'-tsRNA was completely suppressed by the aak-2 mutation, and the aak-2 is known as a gene required for DR-mediated lifespan regulation.

Contrarily, as shown in FIGS. 9C to 9E, it can be seen that when Gln 5'-tsRNA was overexpressed, the lifespan of *C. elegans* having the daf-16 or hsf-1 mutation was independently increased, and it is known that the daf-16 and hsf-1 are not genes generally required for DR-mediated lifespan regulation.

Therefore, summarizing the experimental results, it can be seen that the anti-aging effect caused by Gln 5'-tsRNA acts through the DR/AMPK pathways.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

INDUSTRIAL APPLICABILITY

By not only easily identifying the anti-aging mechanism but also identifying the anti-aging function of tsRNAs, an animal model according to the present invention can be expected to highly contribute to various research fields such as development of new anti-aging drugs, and screening of various factors including an aging-inducing material.

[Sequence Listing Free Text]

<210> 1

<211> 33

<212> DNA

<213> *Caenorhabditis elegans*

<400> 1
ggttccatgg tgtagcggtt agcactcagg act

<210> 2

<211> 30

<212> DNA

<213> Artificial Sequence

<220>

<223> Glutamine tRNA 5' terminal probe

<400> 2
cctgagtgct aaccgctaca ccatggaacc

<210> 3

<211> 30

<212> DNA

<213> Artificial Sequence

<220>

<223> Glutamine tRNA 3' terminal probe

-continued

[Sequence Listing Free Text]

<400> 3
tggaggttcc accgagattt gaactcgggt

<210> 4

<211> 36

<212> DNA

<213> Artificial Sequence

<220>

<223> Forward U6p

<400> 4
cgggaattcc tccaagaact cgtacaaaaa tgctct

<210> 5

<211> 65

<212> DNA

<213> Artificial Sequence

<220>

<223> Reverse U6p-Gln tsRNA

<400> 5
agtcctgagt gctaaccgct acaccatgga accaaacatt tagatttgca attcaattat atagg

<210> 6

<211> 60

<212> DNA

<213> Artificial Sequence

<220>

<223> Forward Gln tsRNA-U6UTR

<400> 6
ggttccatgg tgtagcggtt agcactcagg actcaataat attctagata tcccttttg

<210> 7

<211> 31

<212> DNA

<213> Artificial Sequence

<220>

<223> Reverse U6UTR

<400> 7
cggaagcttc acagccgact atgtttggcg t

SEQUENCE LISTING

```
<160> NUMBER OF SEQ ID NOS: 7

<210> SEQ ID NO 1
<211> LENGTH: 33
<212> TYPE: DNA
<213> ORGANISM: Caenorhabditis elegans

<400> SEQUENCE: 1

ggttccatgg tgtagcggtt agcactcagg act                                   33


<210> SEQ ID NO 2
<211> LENGTH: 30
<212> TYPE: DNA
<213> ORGANISM: Artificial
<220> FEATURE:
<223> OTHER INFORMATION: Glutamine tRNA 5' terminal probe

<400> SEQUENCE: 2

cctgagtgct aaccgctaca ccatggaacc                                       30


<210> SEQ ID NO 3
<211> LENGTH: 30
<212> TYPE: DNA
<213> ORGANISM: Artificial
<220> FEATURE:
<223> OTHER INFORMATION: Glutamine tRNA 3' terminal probe

<400> SEQUENCE: 3

tggaggttcc accgagattt gaactcgggt                                       30


<210> SEQ ID NO 4
<211> LENGTH: 36
<212> TYPE: DNA
<213> ORGANISM: Artificial
<220> FEATURE:
<223> OTHER INFORMATION: Forward U6p

<400> SEQUENCE: 4

cgggaattcc tccaagaact cgtacaaaaa tgctct                                36


<210> SEQ ID NO 5
<211> LENGTH: 65
<212> TYPE: DNA
<213> ORGANISM: Artificial
<220> FEATURE:
<223> OTHER INFORMATION: Reverse U6p-Gln tsRNA

<400> SEQUENCE: 5

agtcctgagt gctaaccgct acaccatgga accaaacatt tagatttgca attcaattat      60

atagg                                                                  65


<210> SEQ ID NO 6
<211> LENGTH: 60
<212> TYPE: DNA
<213> ORGANISM: Artificial
<220> FEATURE:
<223> OTHER INFORMATION: Forward Gln tsRNA-U6UTR

<400> SEQUENCE: 6

ggttccatgg tgtagcggtt agcactcagg actcaataat attctagata tcccttttg      60


<210> SEQ ID NO 7
<211> LENGTH: 31
<212> TYPE: DNA
<213> ORGANISM: Artificial
```

-continued

```
<220> FEATURE:
<223> OTHER INFORMATION: Reverse U6UTR

<400> SEQUENCE: 7

cggaagcttc acagccgact atgtttggcg t                                    31
```

The invention claimed is:

1. A transgenic *Caenorhabditis elegans* (*C. elegans*) whose genome comprises a nucleic acid encoding glutamine tRNA 5', wherein said *C. elegans* has an increased lifespan compared to a wild-type *C. elegans* and where said nucleic acid consists of the sequence set forth in SEQ ID NO: 1.

2. The transgenic *C. elegans* of claim 1, which is for an anti-aging animal model.

3. The transgenic *C. elegans* of claim 1, which exhibits an anti-aging effect due to mitochondrial activation.

4. The transgenic *C. elegans* of claim 1, which exhibits an anti-aging effect via dietary restriction (DR)/AMP-dependent kinase (AMPK) pathways.

5. A method of producing the transgenic *C. elegans* of claim 1, the method comprising:

(a) constructing a recombinant vector including a U6 promoter, Gln 5'-tsRNA DNA and an U6 3' untranslated region (UTR); and (b) injecting the recombinant vector into *C. elegans.*

6. The method of claim 5, wherein the injection in step (b) is done by microinjection.

* * * * *